(12) United States Patent
Sugimura et al.

(10) Patent No.: US 7,939,296 B2
(45) Date of Patent: May 10, 2011

(54) METHOD FOR PRODUCTION OF RECOMBINANT HUMAN FSH

(75) Inventors: Atsushi Sugimura, Shiga (JP); Katsuya Daimon, Kyoto (JP); Kazutoshi Mihara, Hyogo (JP); Yae Ito, Hyogo (JP)

(73) Assignee: JCR Pharmaceuticals Co., Ltd., Ashiya-shi (JP)

( * ) Notice: Subject to any disclaimer, the term of this patent is extended or adjusted under 35 U.S.C. 154(b) by 0 days.

(21) Appl. No.: 12/466,652

(22) Filed: May 15, 2009

(65) Prior Publication Data

US 2009/0291473 A1 Nov. 26, 2009

(30) Foreign Application Priority Data

May 16, 2008 (JP) ................ P2008-129254

(51) Int. Cl.
*C12N 15/09* (2006.01)
*A23J 1/00* (2006.01)
(52) U.S. Cl. ........ 435/69.4; 435/397; 435/398; 530/412
(58) Field of Classification Search ............. 435/69.4, 435/397, 398; 530/412
See application file for complete search history.

(56) References Cited

U.S. PATENT DOCUMENTS

| 4,923,805 | A | 5/1990 | Reddy et al. | |
|---|---|---|---|---|
| 5,990,288 | A | 11/1999 | Musick et al. | |
| 7,517,242 | B2 | 4/2009 | Brodersen et al. | |
| 7,741,455 | B2 * | 6/2010 | Valax et al. | 530/412 |

FOREIGN PATENT DOCUMENTS

| JP | 7024584 | B | 3/1995 |
|---|---|---|---|
| JP | 2523843 | B2 | 8/1996 |
| JP | 2559196 | B2 | 12/1996 |
| JP | 2001323000 | A | 11/2001 |
| JP | 2001323000 | W | 11/2001 |
| JP | 2006109696 | A | 4/2006 |
| WO | 8604589 | A1 | 8/1986 |
| WO | 8810270 | A1 | 12/1988 |
| WO | 2005063811 | A1 | 7/2005 |
| WO | 2006051070 | A1 | 5/2006 |
| WO | 2007065918 | A2 | 6/2007 |

OTHER PUBLICATIONS

Fiddes, J.C. and H.M. Goodman. "The cDNA for the Beta-subunit of human chorionic gonadotropin suggests evolution of a gene by readthrough into the 3'-untranslated region." (Nature), Aug. 14, 1980, 684-687, 286.

Hakola, K., et al. "Recombinant rat follicle-stimulating hormone; production by Chinese hamster ovary cells, purification and functional characterization." Molecular and Cellular Endocrinology, vol. 127, p. 59-69, (1997).

Hjorth, R., et al. "Chromatography for Downstream Processing of Therapeutic Proteins—Current Status and Future Challenges." AIChE Annu. Meet. Proc. Abst., (2006).

Lynch, S., et al. "The extraction and purification of human pituitary follicle-stimulating hormone and luteinizing hormone." Acta Endocrinologica, vol. 288, p. 12-19, (1998).

\* cited by examiner

*Primary Examiner* — Tekchand Saidha

(74) *Attorney, Agent, or Firm* — Millen, White, Zelano, Branigan, P.C.

(57) ABSTRACT

Disclosed is a method for production of recombinant human FSH in high yield and a high purity. The method comprises the steps of: (a) culturing recombinant human FSH-producing mammalian cells in a serum-free medium, (b) collecting culture supernatant, (c) subjecting the culture supernatant to cation-exchange column chromatography, (d) dye affinity column chromatography, (e) hydrophobic column chromatography, and (f) gel filtration column chromatography to collect recombinant human FSH-active fractions, in the order.

7 Claims, 12 Drawing Sheets

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial
<220> FEATURE:
<223> OTHER INFORMATION: Primer Hyg-Sfi

<400> SEQUENCE: 1
gaggccgcct cggcctctga                                              20

<210> SEQ ID NO 2
<211> LENGTH: 29
<212> TYPE: DNA
<213> ORGANISM: Artificial
<220> FEATURE:
<223> OTHER INFORMATION: Primer Hyg-BstX

<400> SEQUENCE: 2
aaccatcgtg atgggtgcta ttcctttgc                                    29
```

<210> SEQ ID NO 3
<211> LENGTH: 20
<212> TYPE: DNA
<213> ORGANISM: Artificial
<220> FEATURE:
<223> OTHER INFORMATION: Primer HCG-A-F

<400> SEQUENCE: 3
atcctgcaaa aagcccagag                                          20

<210> SEQ ID NO 4
<211> LENGTH: 20
<212> TYPE: DNA
<213> ORGANISM: Artificial
<220> FEATURE:
<223> OTHER INFORMATION: Primer HCG-A-R

<400> SEQUENCE: 4
cttgaagcgt gtcaaagtgg                                          20

<210> SEQ ID NO 5
<211> LENGTH: 30
<212> TYPE: DNA
<213> ORGANISM: Artificial
<220> FEATURE:
<223> OTHER INFORMATION: Primer HCGA-ORF-F

<400> SEQUENCE: 5
gcgaattcgc caccatggat tactacagaa                               30

<210> SEQ ID NO 6
<211> LENGTH: 25
<212> TYPE: DNA
<213> ORGANISM: Artificial
<220> FEATURE:
<223> OTHER INFORMATION: Primer HCGA-ORF-R

<400> SEQUENCE: 6
gcgaattctt aagatttgtg ataat                                    25

<210> SEQ ID NO 7
<211> LENGTH: 20
<212> TYPE: DNA
<213> ORGANISM: Artificial
<220> FEATURE:
<223> OTHER INFORMATION: Primer FSH-F

<400> SEQUENCE: 7
gaccacaggt gagtcttggc                                          20

<210> SEQ ID NO 8
<211> LENGTH: 20
<212> TYPE: DNA
<213> ORGANISM: Artificial
<220> FEATURE:
<223> OTHER INFORMATION: Primer FSH-R

<400> SEQUENCE: 8
tggtccttca ggacaagggt                                          20

<210> SEQ ID NO 9
<211> LENGTH: 30
<212> TYPE: DNA
<213> ORGANISM: Artificial
<220> FEATURE:
<223> OTHER INFORMATION: Primer FSH-F2

```
<400> SEQUENCE: 9
gcgaattcgc caccatgaag acactccagt                              30

<210> SEQ ID NO 10
<211> LENGTH: 30
<212> TYPE: DNA
<213> ORGANISM: Artificial
<220> FEATURE:
<223> OTHER INFORMATION: Primer FSH-R2

<400> SEQUENCE: 10
taagaatgcg gccgcccact gatctttatt                              30
```

METHOD FOR PRODUCTION OF RECOMBINANT HUMAN FSH

FIELD OF THE INVENTION

The present invention relates to a method for production of recombinant human FSH, more specifically to a method for production of recombinant human FSH by culturing recombinant human FSH-producing mammalian cells in a serum-free medium, as well as to a method for production through purification of recombinant human FSH which is obtained in the culture supernatant, in high yield and to such a high purity that allows its direct use as a medicament.

BACKGROUND OF THE INVENTION

Follicle-stimulating hormone (FSH) is a glycoprotein having a molecular weight of 34 kD, which consists of two subunits, $\alpha$ and $\beta$, and has an activity to promote production of estrogen in the ovary and its secretion from it. Medical drugs containing human FSH as their principal agent are used in infertility treatment. At first, the human FSH contained in them a protein which was obtained through purification from human urine. Recently, recombinant human FSH produced making use of the genetic recombination technology was approved for sale and has been used as a therapeutic drug for infertility treatment with indications for "controlled ovarian stimulation for growth of multiple follicles" and "induction of ovulation in cases of anovulation or infrequent ovulation accompanying hypothalamic-pituitary dysfunction".

The genes encoding the $\alpha$- and the $\beta$-subunits of human FSH have been cloned, of which the $\alpha$-subunit is a protein that is identical to the $\alpha$-subunit of human chorionic gonadotropin (hCG) (see patent document 1 and non-patent document 1).

A method for production of recombinant human FSH has been disclosed in which mammalian cells (such as CHO cells) were employed that had been transformed with expression vectors having incorporated genes encoding one or the other of the two subunits of human FSH (see patent document 2). According to the document, the genes encoding the two subunits of human FSH were separately incorporated into different expression vectors, which then were introduced into the same CHO cells. And, the two subunits, separately expressed by those expression vectors, form a hetero dimer within the cell, thereby giving active human FSH. However, the document contains no specific description as to how the human FSH is purified.

A method for purification of recombinant human FSH has been disclosed in a publication, in which culture supernatant of recombinant human FSH producing cells cultured in either a serum-containing or a serum-free medium, was subjected to sequential chromatography using a blue-dye, a hydrophobic, and then a reverse-phase column in the order (see patent document 3). The document also discloses a method for purification of recombinant human FSH, in which anion-exchange column chromatography was additionally employed following the above chromatography procedure. In both of these methods, 2-propanol is used to elute FSH from the reverse-phase column. Organic solvents such as 2-propanol, however, may denature proteins, and, further, their use in an industrial-scale production is economically disadvantageous, for such organic solvents are unfavorable to the environment and therefore require a facility in which to treat the waste fluid containing them.

Further, a method for purification of recombinant human FSH has been disclosed in a publication, in which chromatography using an anion-exchange, an immobilized metal ion adsorption, a hydrophobic, and then a reverse phase column is employed in the order (see patent document 4). As it employs 2-propanol, too, to elute the recombinant human FSH from the reverse-phase column, this method is not desirable either to the environment or in the economic sense for the same reason as is mentioned above. Furthermore, though it is for urine-derived human FSH, another method has also been disclosed in a publication in which purification of human FSH is performed by chromatography using an anti-human FSH antibody affinity column and then a reverse-phase column (see patent document 5). This method, however, also has the same disadvantage as in those methods mentioned above, for it also employs 2-propanol to elute human FSH from a reverse-phase column.

On the other hand, a method has been disclosed for purification of recombinant human FSH without using any organic solvent. The method utilizes chromatography employing a dye affinity, a weak ion-exchange, a hydrophobic, a strong ion-exchange, and then a hydrophobic column in the order (patent document 6). The examples presented in the document, however, are not of wild-type human FSH but only of those of mutant-type proteins which were formed by incorporating a fragment of another amino acid sequence into human wild-type FSH.

In addition, through a method has been known for purification of human FSH from human urine (patent document 7), the method involves a process in which an organic solvent (ethanol) is employed, and therefore has the same disadvantage as is mentioned above.

[Patent document 1] Japanese Patent No. 2008344
[Patent document 2] Japanese Patent No. 2559196
[Patent document 3] WO 2006/051070
[Patent document 4] WO 2005/063811
[Patent document 5] Japanese Patent No. 2523843
[Patent document 6] WO 2007/065918
[Patent document 7] Japanese Patent Application Publication No. 2001-323000
[Non-patent document 1] Nature, 286: 684-687 (1980)

SUMMARY OF THE INVENTION

Against the above background, it is the objective of the present invention to provide a method for purification of recombinant human FSH starting with the supernatant of the culture of recombinant human FSH-producing cells, in high yield and to such a purity as allows its direct use as a medicament, only through such processes none of which employs an organic solvent.

The present inventors found that recombinant human FSH which is contained in the culture supernatant of recombinant human FSH-producing cells cultured in a serum-free medium, can be purified to a very high purity, and in a very high yield as well, by subjecting the recombinant human FSH to a purification process consisting of a combination of cation-exchange column chromatography, dye affinity column chromatography, hydrophobic column chromatography, and gel filtration column chromatography. The present invention was completed through further studies based on the finding.

Thus, the present invention provides what follows:

1. A method for production of recombinant human FSH comprising the steps of:

(a) culturing recombinant human FSH-producing mammalian cells in a serum-free medium to let them secrete recombinant human FSH in the medium, (b) collecting culture supernatant by removing the cells from the culture that is obtained in step (a) above, (c) subjecting the culture supernatant collected in step (b) above to cation-exchange column chromatography to collect recombinant human FSH-active fractions, (d) subjecting the fractions collected in step (c) above to dye affinity column chromatography to collect recombinant human FSH-active fractions, (e) subjecting the fractions collected in step (d) above to hydrophobic column chromatography to collect recombinant human FSH-active fractions, and (f) subjecting the fractions collected in step (e) above to gel filtration column chromatography to collect recombinant human FSH-active fractions, in the order.

2. The method according to (1) above, wherein the ion exchanger employed in the cation-exchange column chromatography is a weak cation exchanger.

3. The method according to (2) above, wherein the weak cation exchanger has a selectivity based on both hydrophobic interaction and hydrogen bond formation.

4. The method according to (2) or (3) above, wherein the weak cation exchanger has phenyl groups, amide bonds and carboxyl groups.

5. The method according to one of (1) to (4) above, wherein the dye employed in the dye affinity column chromatography is a blue triazine dye.

As it allows to produce recombinant human FSH starting with serum-free culturing of cells, the present invention provides recombinant human FSH which is free of any serum-derived contaminants such as viruses or prions. Therefore, the recombinant human FSH obtained according to the present invention can be administered into a human body as a safe medicament for infertility treatment which is completely free of any risks of infection with those infectious agents. Further, as it allows purification of recombinant human FSH without using an organic solvent, the present invention eliminates the risk of denaturation of recombinant human FSH which might otherwise occur due to the exposure of it to an organic solvent employed. Furthermore, the present invention is favorable to the environment, for the waste fluid left after performing the purification process according to it does not contain an organic solvent, and in the economic sense as well, for it requires no facility in which to treat organic solvents which would otherwise be contained in the waste fluid.

DETAILED DESCRIPTION OF THE INVENTION

Figure 1A:
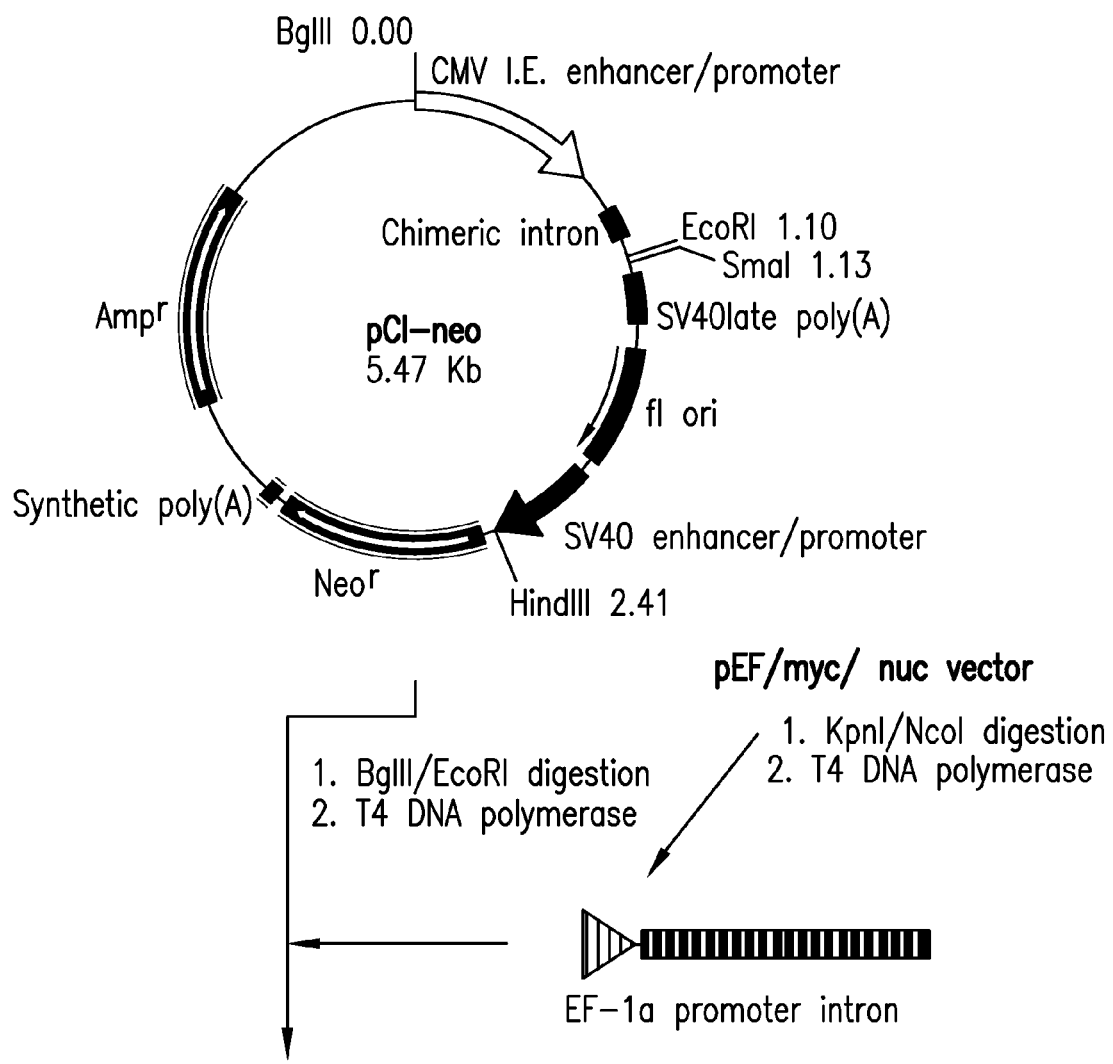
FIG. 1A shows a flow diagram illustrating the method for construction of vector pE-neo.

In the present invention, the term "recombinant human FSH-producing mammalian cells" means mammalian cells which have been artificially manipulated to express, or strongly express, the genes that encode the two subunits, β and β, of human FSH. Though in general the genes to be strongly expressed are those which are introduced to the mammalian cells for transformation using expression vectors in which those genes are incorporated, they may be also intrinsic genes which have undergone artificial modification to let them be strongly expressed. Examples of the means for artificially modifying an intrinsic gene to let it be strongly expressed include, but not limited to, replacing the promoter upstream of the intrinsic gene with a promoter which strongly induces expression of the gene. Though there is no particular limitation as to which mammalian cells are to be employed, preferred are those of human-, mouse- or hamster-origin, and, among others, CHO cells, which originate from Chinese hamster ovary cells, are particularly preferred.

In the present invention, the term "recombinant human FSH" means the human FSH which the above-mentioned recombinant human FSH-producing mammalian cells secrete in the medium during culture.

In the present invention, an example of preferable serum-free media in which the recombinant human FSH-producing mammalian cells are to be cultured is the following medium which contains:

| | |
|---|---|
| Amino acids | 3-700 mg/L |
| Vitamins | 0.001-50 mg/L |
| Monosaccharides | 0.3-10 g/L |
| Inorganic salts | 0.1-10000 mg/L |
| Trace elements | 0.001-0.1 mg/L |
| Nucleosides | 0.1-50 mg/L |
| Fatty acids | 0.001-10 mg/L |
| Biotin | 0.01-1 mg/L |
| Hydrocortisone | 0.1-20 µg/L |
| Insulin | 0.1-20 mg/L |
| Vitamin $B_{12}$ | 0.1-10 mg/L |
| Putrescine | 0.01-1 mg/L |
| Sodium pyruvate | 10-500 mg/L, and |

Water-soluble iron compounds. As desired, it may also include thymidine, hypoxanthine, a conventional pH indicator, and antibiotics.

Further, DMEM/F12 medium, a mixture medium consisting of DMEM and F12, may be used as a basic serum-free medium. Both of these media are well known to those skilled in the art. As a serum-free medium, DMEM(HG)HAM modified (R5) medium may be used, which includes sodium hydrogen carbonate, L-glutamine, D-glucose, insulin, sodium selenite, diaminobutane, hydrocortisone, ferric (II) sulfate, asparagine, aspartic acid, serine, and polyvinyl alcohol. Furthermore, a commercially available serum-free medium may also be used as a basic medium, such as CDoptiCHO, CHO-S-SFM II or CD CHO (Invitrogen), IS CHO-V or IS CHO-V-GS (Irvine), EX-CELL302 or EX-CELL305 (JRH), or the like.

Each of the chromatography procedures for purification of the recombinant human FSH may, when needed, be carried out in the presence of a nonionic surfactant in order to prevent nonspecific binding of the protein. Though there is no particular limitation as to which nonionic surfactant is to be employed, preferably a polysorbate-based surfactant, more preferably polysorbate 80, is employed. The concentration of such nonionic surfactant is preferably 0.005% (w/v) to 0.015% (w/v), more preferably 0.01% (w/v).

The process for purification of the human FSH may be carried out at room temperature or at lower temperatures, but preferably at lower temperatures, particularly at 1-10° C.

In the process of the first chromatography for the purification, the recombinant human FSH is let bind to the cationic-exchange column that has been equilibrated with a phosphate buffer supplemented with a salt. The pH of this phosphate buffer has been adjusted preferably to 5-6.5, more preferably to about 5.5-6.0. Though there is no particular limitation as to which salt is to be added to the phosphate buffer, sodium chloride is preferred, and its concentration is preferably 50-250 mM.

After the column carrying the bound recombinant human FSH is washed, the recombinant human FSH is eluted with a phosphate buffer with an increased concentration of the salt. The pH of the phosphate buffer used in this process is preferably 5.5-6.5, and more preferably about 6.0. And though there is no particular limitation as to which salt it to be added to the phosphate buffer, sodium chloride is preferred, and its concentration is preferably 300-900 mM, and more preferably 400-800 mM.

Further, though there is no particular limitation as to which cation-exchanger is to be employed in the cation-exchange column chromatography, a weak cation exchanger is preferred, and more preferred is a weak cation exchanger having a selectivity based on both hydrophobic interaction and hydrogen bond formation. For example, a weak cation exchanger having phenyl groups, amide bonds and carboxyl groups and having a selectivity based on both hydrophobic interaction and hydrogen bond formation, such as CaptoMMC (GE Healthcare), etc., may be employed.

The dye affinity chromatography, the second process of the purification, is a process for removing contaminants making use of the strong affinity of human FSH to certain dyes. Blue triazine dye is preferably used, but other triazine dyes are also suitable. Particularly preferred is Blue Sepharose 6 FF, Fast Flow (GE Healthcare) in which dye Cibacron™ Blue F3GA is covalently immobilized to Sepharose 6 Fast Flow matrix.

The dye affinity chromatography column is equilibrated at or near the neutral pH, preferably pH7.8-8.2, with a buffer, and fractions of the eluate obtained in the first process are applied to the column. For this, the fractions of the eluate obtained in the first process are adjusted in advance to or near the neutral pH, preferably at pH7.8-8.2, with a buffer. Elution may be done by increasing the concentration of a salt. Though there is no particular limitation as to which salt is to be employed, potassium chloride is preferred, and its concentration is preferably 1.8-2.2 mol/L, and most preferably about 2 mol/L.

The hydrophobic chromatography, the third process of the purification, is a process to eliminate contaminant proteins and the like. Though there is no particular limitation as to which hydrophobic chromatography resin is to be employed, Phenyl-Sepharose may be used preferably.

The salt concentration of the human FSH-containing fractions to be applied to the hydrophobic chromatography must have been adjusted in advance. Though there is no particular limitation as to which salt is to be employed in this process, sodium chloride or potassium chloride are preferred. The concentration of such a salt is preferably 2.5-3.5 mol/L, more preferably 2.8-3.2 mol/L, calculated as sodium chloride concentration. The column must have been to be adjusted to or near the neutral pH, preferably at pH7.8-8.2, more preferably about 8, with a buffer supplemented with a salt. Though there is no particular limitation as to which salt is to be employed for this, sodium chloride is preferred, and its concentration is preferably 2-3 mol/L, more preferably 2.3-2.7 mol/L, and most preferably about 2.5 mol/L.

Elution may be done by decreasing the concentration of the salt. Though there is no particular limitation as to which salt is to be employed, sodium chloride is preferred, and its concentration is preferably 1.2-1.8 mol/L, and more preferably about 1.4-1.6 mol/L.

The gel filtration column chromatography, the forth process of the purification, is a process for elimination of low molecular-weight impurities, such as endotoxins, as well as multimeric complexes or decomposition products of human FSH, and the process thus gives substantially pure human FSH.

EXAMPLES

The present invention is described in further detail below with reference to examples. However, it is not intended that the present invention be limited to the examples.

[Construction of Human FSH Expression Vector]

Vector pEF/myc/nuc (Invitrogen) was digested with KpnI and NcoI to cut out a region including the EF-1α promoter and its first intron, which then was blunt-ended with T4 DNA polymerase. Vector pCl-neo (Invitrogen) was digested with BglII and EcoRI to cut out a region including the CMV enhancer/promoter and the intron, which then was blunt-ended with T4 DNA polymerase. Into this was inserted the above-mentioned region including the EF-1α promoter and its first intron to give vector pE-neo (FIG. 1-1 and FIG. 1-2).

Figure 1B:
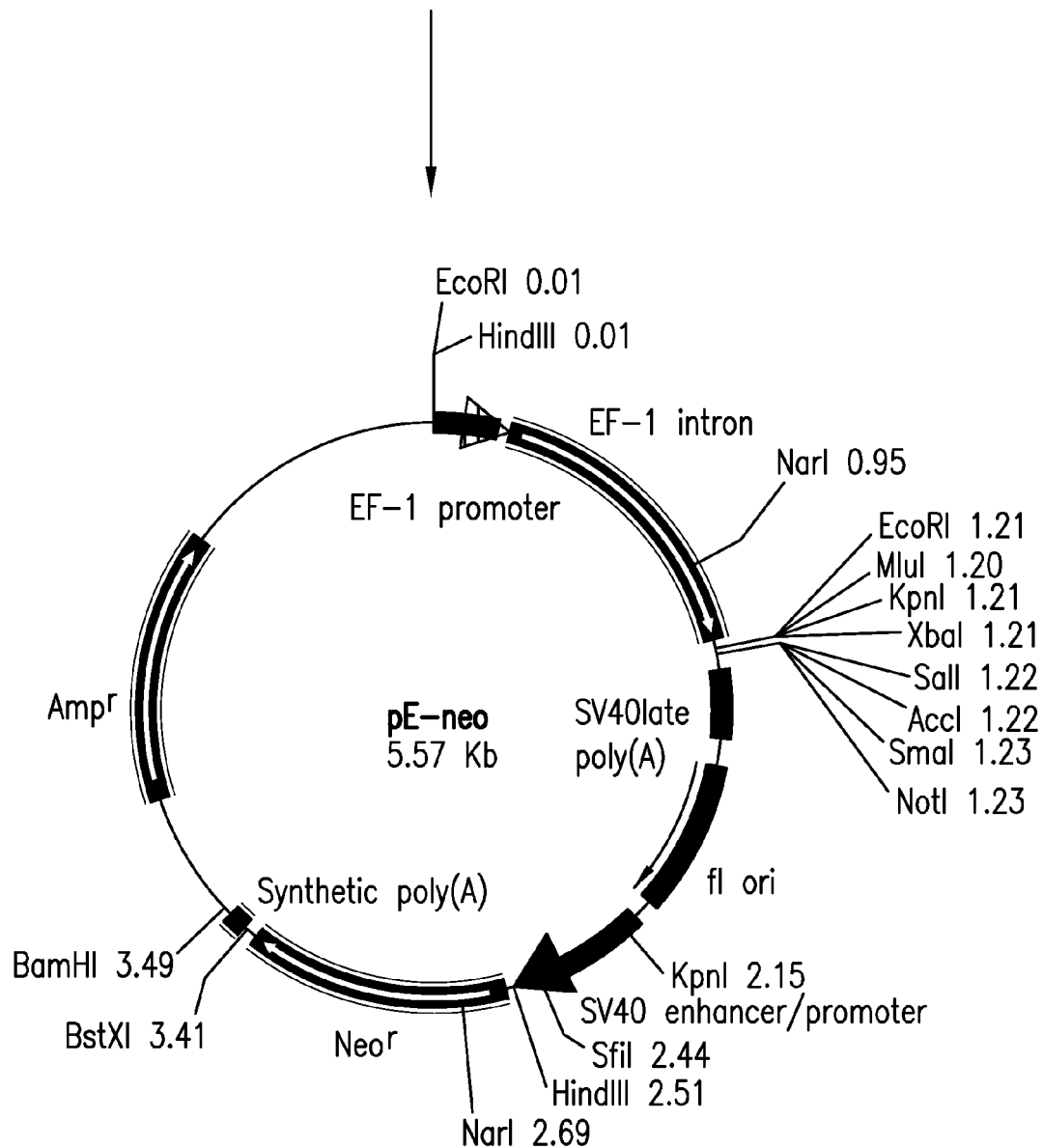
FIG. 1B shows a flow diagram illustrating the method for construction of vector pE-neo.
Figure 2A:
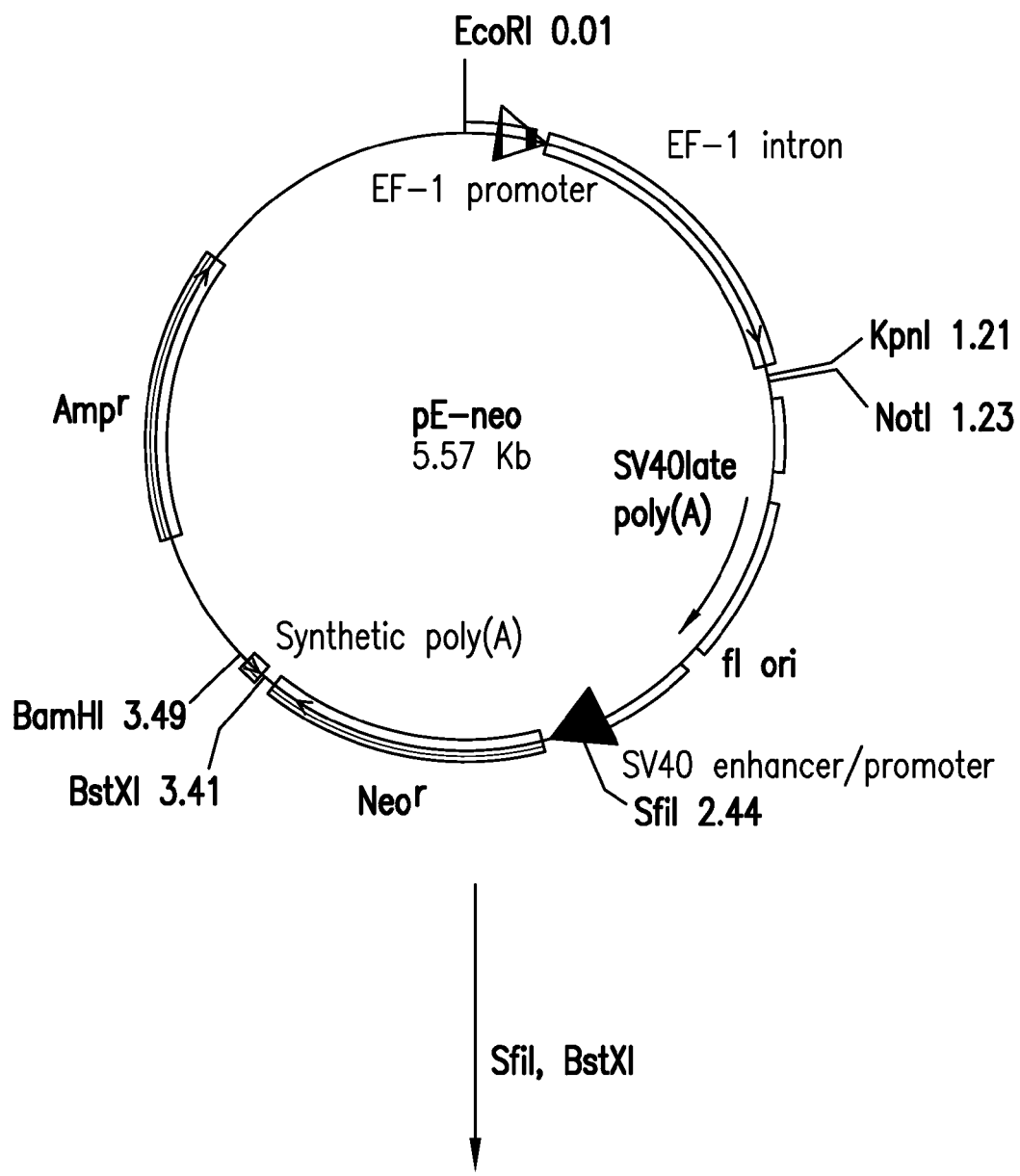
FIG. 2A shows a flow diagram illustrating the method for construction of vector pE-hygr.
Figure 2B:
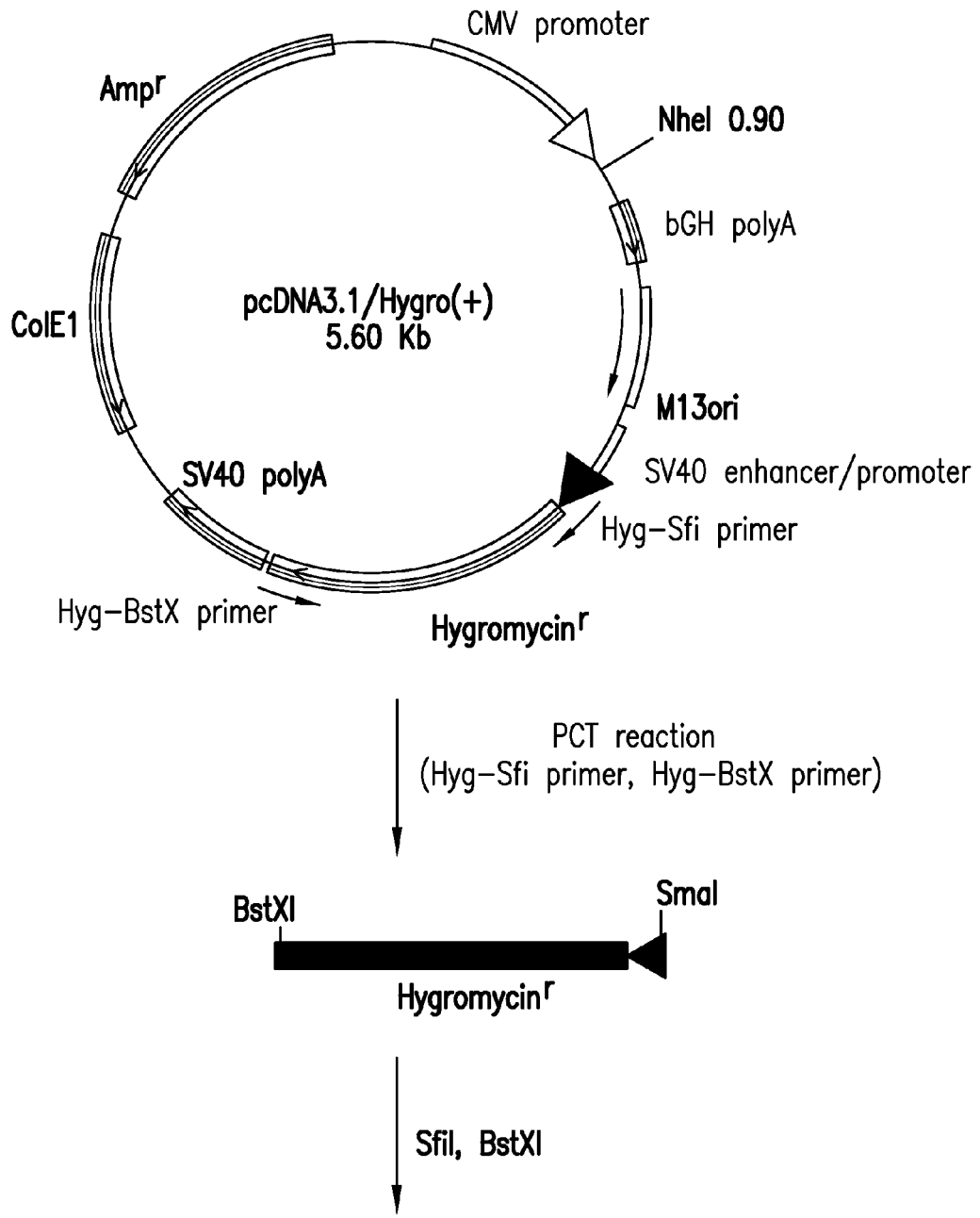
FIG. 2B shows a flow diagram illustrating the method for construction of vector pE-hygr.
Figure 2C:
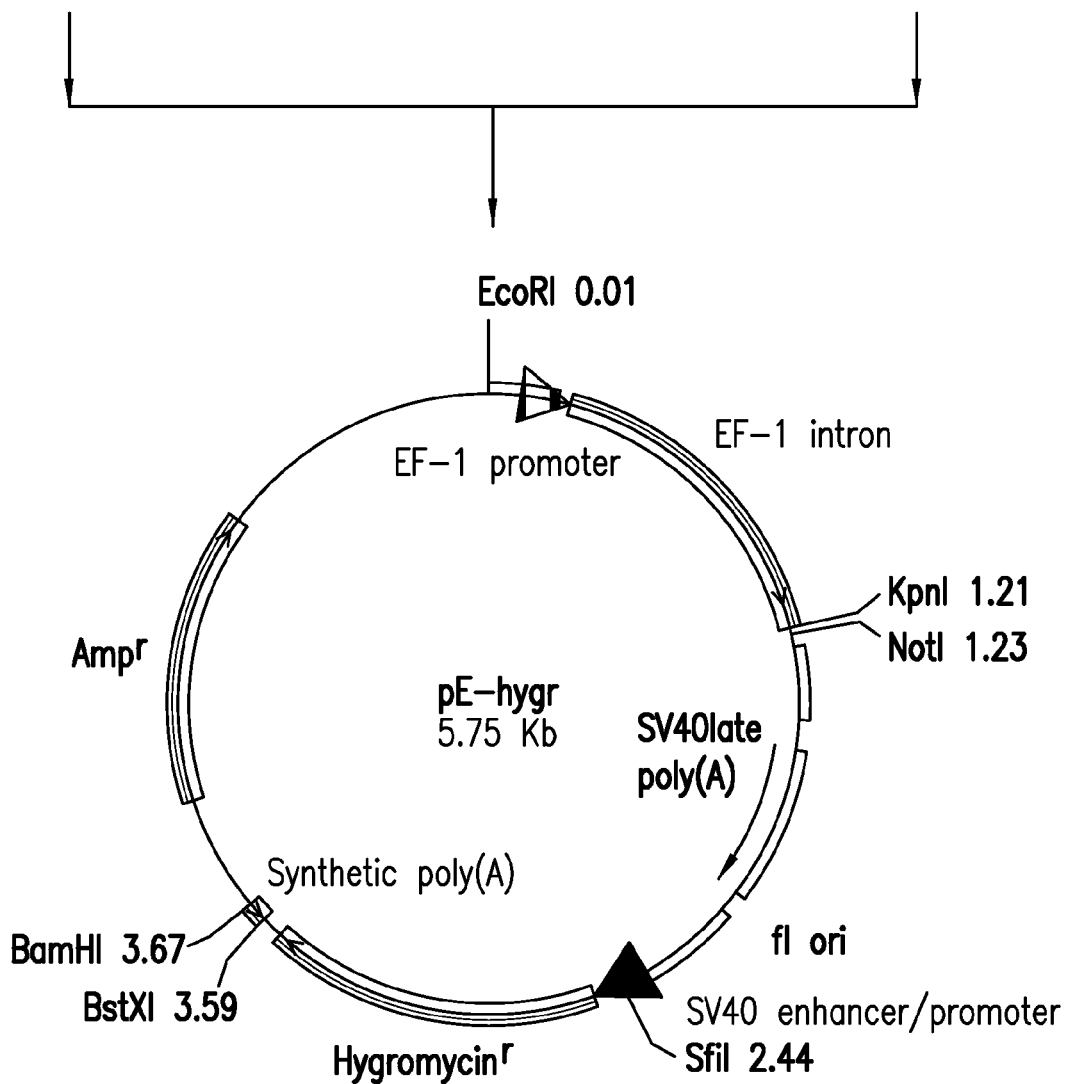
FIG. 2C shows a flow diagram illustrating the method for construction of vector pE-hygr.
Figure 3:
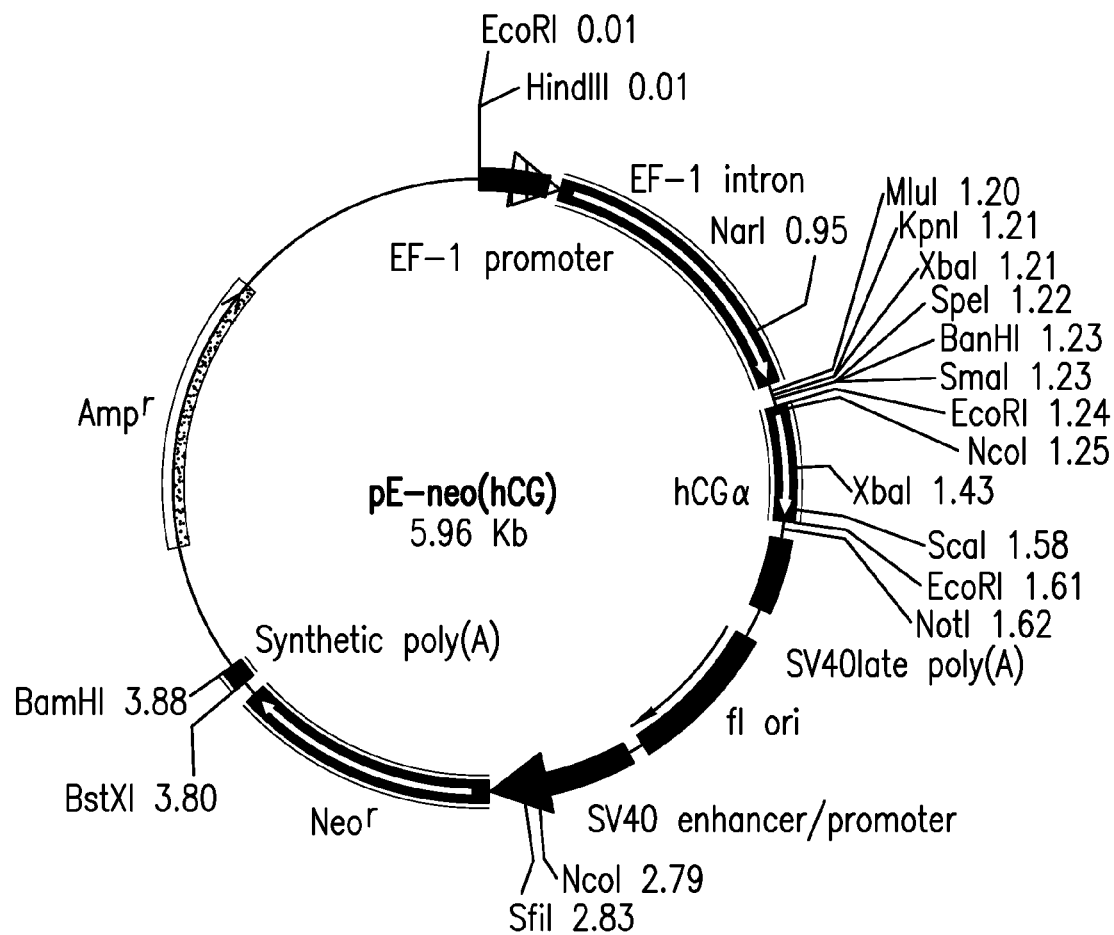
FIG. 3 shows the structure of human FSH α-chain expression vector pE-neo(hCGα).

The vector pE-neo was digested with SfiI and BstXI to remove a region of about 1 kbp including the neomycin resistance gene (FIG. 2-1). Using pcDNA3.1/Hygro(+) (Invitrogen) as a template, the hygromycin gene was amplified by PCR with primer Hyg-Sfi (5'-GAGGCCGCCTCGGC-CTCTGA-3'; SEQ ID NO: 1) and primer Hyg-Bstx (5'-AAC-CATCGTGATGGGTGCTATTCCTTTGC-3'; SEQ ID NO:2) (FIG. 2-2). The hygromycin gene thus amplified was digested with SfiI and BstXI, and then inserted into the aforementioned vector pE-neo to form vector pE-hygr (FIG. 2-3).

Using a human placenta cDNA library (Takara Bio) as a template, a primary PCR was performed with primer HCG-A-F (5'-ATCCTGCAAAAAGCCCAGAG-3'; SEQ ID NO:3) and primer HCG-A-R (5'-CTTGAAGCGTGT-CAAAGTGG-3'; SEQ ID NO:4). Then, using the PCR product which was thus obtained, a secondary PCR was performed to amplify the human FSHα chain cDNA, with primer HCGA-ORF-F (5'-GCGAATTCGCCACCATGGATTAC-TACAGAA-3'; SEQ ID NO:5), which had in its 3'-end region a sequence located a little downstream of primer HCG-A-F used in the primary PCR, and with primer HCGA-ORF-R (5'-GCGAATTCTTAAGATTTGTGATAAT-3'; SEQ ID NO:6), which had in its 5'-end region a sequence located a little upstream of primer HCG-A-R used in the primary PCR. And in the same manner, using a human pituitary gland cDNA library (Takara Bio) as a template, PCR was performed to amplify the human FSHβ chain cDNA, with primary primers FSH-F (5'-GACCACAGGTGAGTCTTGGC-3'; SEQ ID NO:7) and FSH-R (5'-TGGTCCTTCAGGACAAGGGT-3': SEQ ID NO:8) and then secondary primers FSH-F2 (5'-GC-GAATTCGCCACCATGAAGACACTCCAGT-3'; SEQ ID NO:9) and FSH-R2 (5'-TAAGAATGCGGCCGCCCACT-GATCTTTATT-3'; SEQ ID NO: 10).

The primary PCR for human FSHα chain was performed using 100 ng of the human placenta cDNA library as a template and running 40 cycles of reactions each of which consisted of "95° C./10 sec, 55° C./10 sec, and 72° C./10 sec". The secondary PCT was performed using 1 μL of the reaction mixture of the primary PCR as a template and running 30 cycles of reactions each of which consisted of "95° C./10 sec, 60° C./1 sec, and 72° C./1 sec). And, the primary PCR for human FSHβ chain was performed using 10 ng of a human pituitary gland cDNA library as a template and running 40 cycles of reactions each of which consisted of "98° C./2 sec, 60° C./10 sec, and 72° C./10 sec". The secondary PCR was performed using 1 μL of the reaction mixture of the primary PCR as a template and running 30 cycles of reactions each of which consisted of "98° C./2 sec, 60° C./10 sec, 72° C./10 sec".

The human FSHα chain cDNA thus amplified was cleaved with EcoRI and inserted into the EcoRI site of pBluescriptI-ISK(–) (pBS: Stratagene) which had been digested with EcoRI. The plasmid DNA thus obtained was digested with XbaI and EcoRV to cut out human FSHα-chain cDNA, which then was inserted into the vector pE-neo that had been digested with XbaI and SmaI to make human FSHα-chain expression vector pE-neo (hCGα) (FIG. 3).

Figure 4:
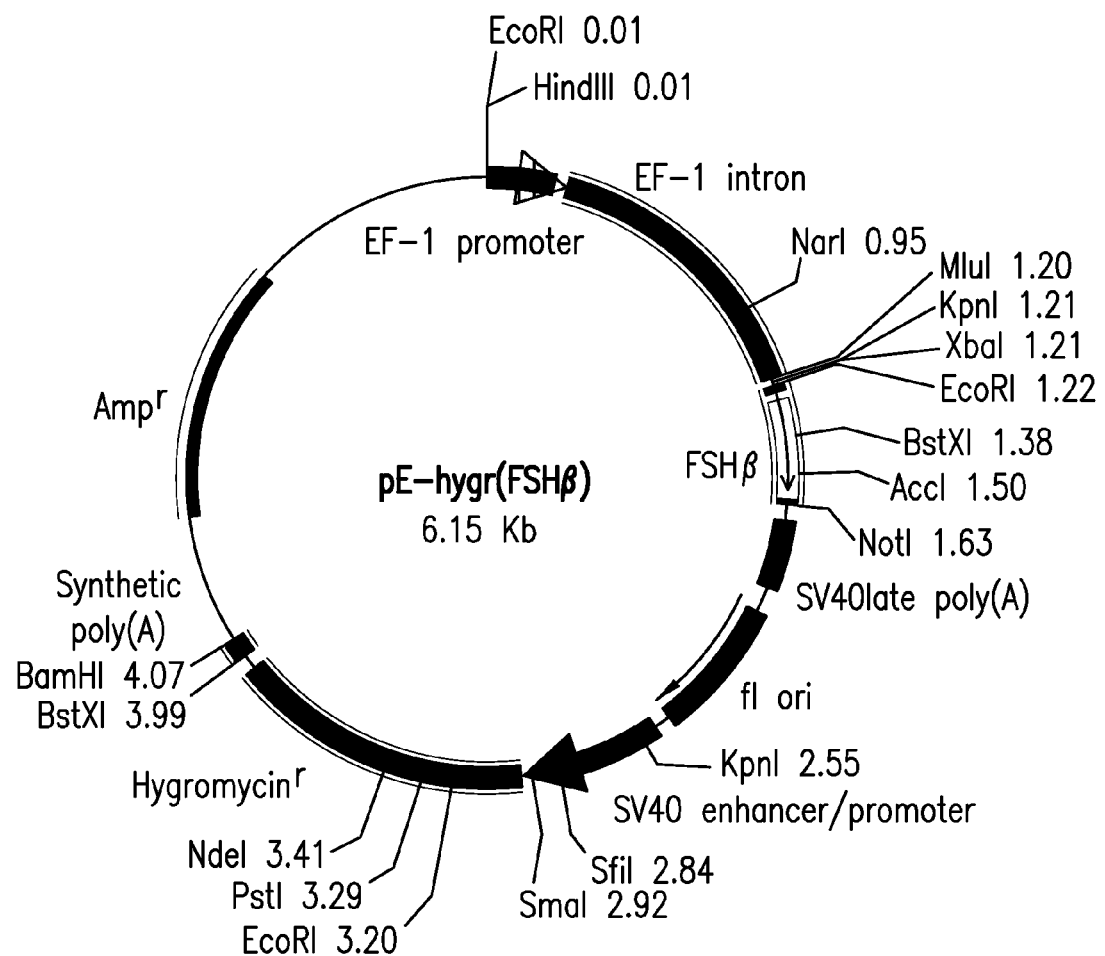
FIG. 4 shows the structure of human FSH β-chain expression vector pE-hygr(FSHβ).

The human FSHβ-chain cDNA amplified above was digested with EcoRI and NotI, and then introduced into pBluescriptIISK(–) which had been digested with EcoRI and NotI. The plasmid DNA thus obtained was digested with EcoRI and, after blunt-ended with T4 DNA polymerase, digested with NotI to cut out human FSHβ-chain cDNA. The vector pE-hygr was digested with XbaI and, after blunt-ended with T4 DNA polymerase, digested with NotI. To this pE-hygr vector was introduced human FSHβ-chain cDNA to make human FSHβ expression vector pE-hygr(FSHβ) (FIG. 4).

[Production of Recombinant Cells for Expression of Human FSH]

CHO cells (CHO-K1: purchased from American Type Culture Collection) was transfected with the above-mentioned expression vector pE-neo(hCGα) and pE-hygr(FSHβ) using Lipofectamine-2000 (Invitrogen) according to the following method. Briefly, on the day before transfection, CHO-K1 cells were seeded in a 3.5-cm culture dish so that a cell density might be close to that of a confluent state, and the cells were cultured overnight at 37° C. under a flow of air containing 5% carbon dioxide. On the following day, the cells were washed twice with PBS(–), and the medium was replaced with 1 mL of serum-free D-MEM/F12 medium (Invitrogen). Two hundred μL of a 1:1 mixture solution consisting of Lipofectamine-2000 solution diluted 20 times with Opti-MEM I medium (Invitrogen) and a plasmid DNA solution (pE-neo (hCGα) 13.2 μg/mL and pE-hygro(FSHβ) 6.6 μg/mL) was added, and transfection was performed at 37° C. for five hours.

After transfection, the medium was replaced with D-MEM/F12 medium containing 5% FCS (D-MEM/F12/5% FCS), and culture was carried out for 2 days at 37° C. under a flow of air containing 5% carbon dioxide. The medium then was replaced with the D-MEM/F12/5% FCS medium containing 0.6 mg/mL G418 and 0.4 mg/mL hygromycin B, and selective culture was carried out at 37° C. under a flow of air containing 5% carbon dioxide. Cells that had grown in the medium for selective culture were subjected to several successive rounds of subculture in the medium to give recombinant cells.

Then, according to the limiting dilution technique, the recombinant cells were seeded on a 96-well plate in such a manner that not more than one cell might be seeded per well, and the cells were cultured for about 10 days to let each of them form a clonal colony. The culture supernatant in the wells where a clonal colony was formed was sampled and examined by ELIZA for the amount of expressed FSH, and cell lines which were found expressing a high amount of human FSH were selected.

For habituation to serum-free suspended cell culture, the selected cell lines were cultured in a commercially available serum-free medium, EX-CELL302 medium (JRH) supplemented with 4 mM L-glutamine, 10 mg/L hypoxantine, 4 mg/L thymidine, 120 mg/L G148, 80 mg/L hygromycin B, until the growth rate of the cells stabilized. Then, the medium was replaced with IS CHO-V-GS medium and culture was carried out until the growth rate of the cells stabilized, and the cells were suspended in IS CHO-V-GS medium supplemented with 10% DMSO, and stored as seed cells in liquid nitrogen.

[Culture of Recombinant Cells for Expression of Human FSH]

The above seed cells were thawed and diluted to a density of $2\times10^5$ cells/mL and cultured in IS CHO-V-GS medium for 3 days. The cells then were diluted to a cell density of $2\times10^5$ cells/mL with a medium consisting of 1:1 mixture of IS CHO-V-GS medium and CDoptiCHO(CD) medium (Invitrogen) supplemented with 8 mM of L-glutamine, 10 mg/L of hypoxanthine, 4 mg/L of thymidine, 0.12 mg/mL G418, and 80 mg/L of hygromycin B, and cultured for 4 days, then diluted to a cell density of $2\times10^5$ cells/mL with CD medium and subjected to expansion culture which was performed by static-culture for 4 days at 37° C. under 5% carbon dioxide.

The number of the cells was counted, and the cells were diluted with CD medium to a cell density of $5\times10^5$ cells/mL, and 5 L of this cell-containing liquid was transferred to a culture vessel, in which the cells were shake-cultured for 3 days. Then, 20 L of fresh CD medium was added to the culture vessel, and shake-culture was continued for 3 days. The culture conditions for this were as follows: shaking speed; 60 rpm, pH7.2, dissolved oxygen; 70%, temperature; 37° C., surface airation (air); 500 mL/min, intra-liquid airation ($CO_2$); 50 mL/min, intra-liquid airation ($O_2$); 50 mL/min.

Then, the cell culture in the culture vessel was diluted to a cell density of $2\times10^5$ cells/mL with CD medium free of either G418 or hygromycin B, and 250 L of the cell-containing liquid was transferred to a 250-L culture vessel, in which the cells were shake-cultured for 7 days. The culture conditions for this were as follow: shaking speed; 120 rpm, pH7.2, dissolved oxygen; 70%, temperature; 37° C., surface airation; 10 L/min, intra-liquid airation (air); 250 mL/min, intra-liquid airation ($CO_2$); 2500 mL/min, intra-liquid airation ($O_2$); 2500 mL/min. Sampling was made every day during the culture, and measurement was performed for cell number, survival rate, glucose concentration, lactic acid concentration, and amount of expressed human FSH.

Figure 5:
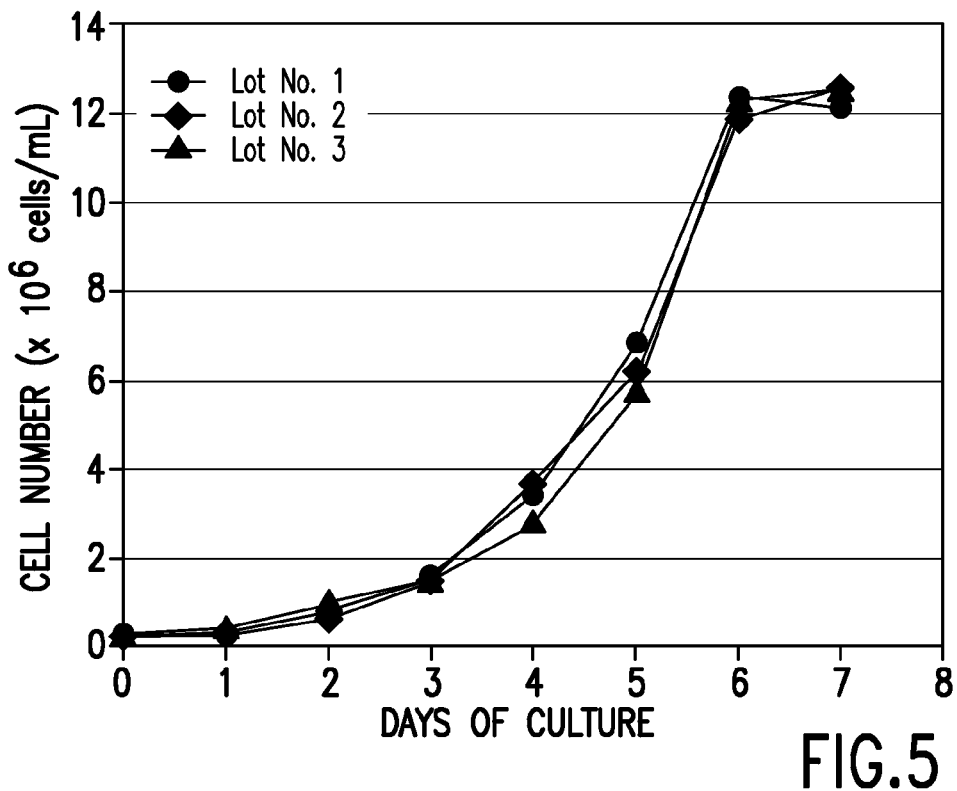
FIG. 5 shows the time course of the viable cell density of recombinant human FSH expressing cells during serum-free culture.
Figure 6:
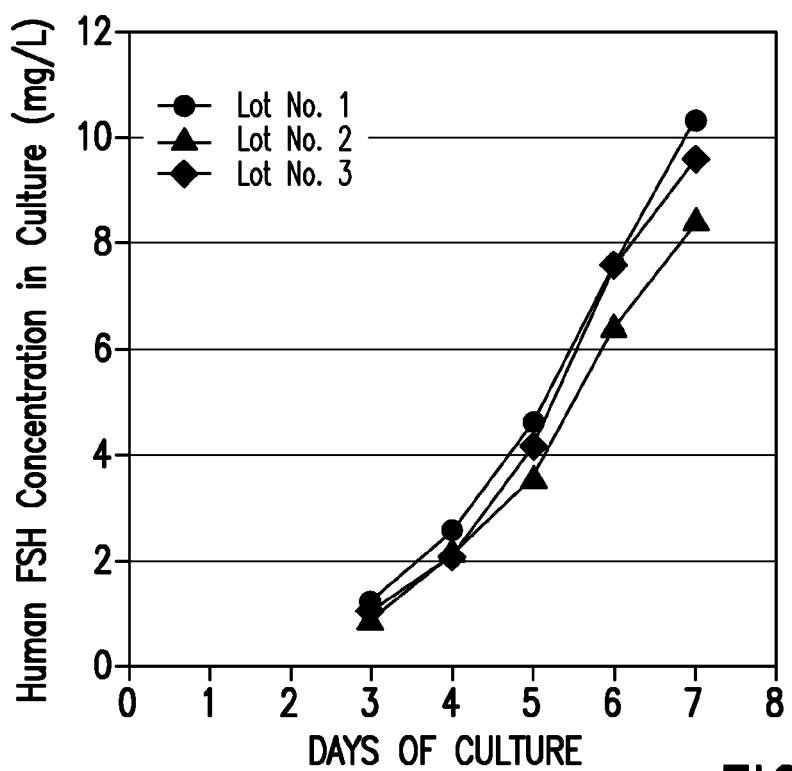
FIG. 6 shows the time course of the concentration of human FSH in the supernatant during serum-free culture.

The above-mentioned cell culture was repeated 3 times (lot Nos. 1-3). In each culture, viable cell density reached about $1\times10^7$ cells/mL or more on days 6-7 of culture, indicating that high-density cell culture was successfully achieved (FIG. 5). ELISA measurement of the concentration of human FSH secreted in the medium by the cells revealed that the concentration increased with a slight time lag from the cell growth curve, reaching about 8-10 mg/L on day 7 of culture (FIG. 6).

The cell culture was collected and, after the cells were removed with Zeta Plus™ filter cartridge 90MZ03M (3M), filtered with a 0.22 µm filter to give a culture supernatant.

[Method for Purification of Human FSH]

To the culture supernatant collected above was added 6N HCl to adjust the pH of the culture supernatant to 5.5, and precipitate was removed by filtration. This culture supernatant was loaded on CaptoMMC column (column volume; about 10 L, bed height; about 20 cm), a cation-exchange column having a selectivity based on both hydrophobic interaction and hydrogen bond formation, which had been equilibrated with 4-fold column volume of 50 mM sodium phosphate/100 mM NaCl (pH5.5) solution, supplied at a linear flow rate of 150 cm/hr, to allow adsorption to take place. Then after the column was washed with 4-fold column volume of 50 mM sodium phosphate/100 mM NaCl (pH5.5) solution, supplied at the same flow rate, the adsorbed protein was eluted with 5-fold column volume of 50 mM sodium phosphate/400 mM NaCl (pH6.0) solution.

Then, as a virus inactivation process, tri-n-butyl phosphate (TNBP) and Tween 80 were added to fractions of the eluate from the above CaptoMMC column so that the final concentrations would be 0.3% (v/v) and 1% (w/v), respectively, and the mixture then was let stand for 6 hours at room temperature.

To the virus-inactivated fractions of the eluate from the CaptoMMC column mentioned above was added about 40% by volume of 250 mM Tris-HCl (pH8.5) to adjust their electric conductivity to about 2.6 S/m. This solution was loaded on a Blue sepharose 6FF column (column volume; about 6 L, bed height; about 20 cm), a dye affinity column, which had been equilibrated with 4-fold column volume of 50 mM Tris-HCl/300 mM NaCl (pH8.0) solution, supplied at a linear flow rate of 60 cm/hr, to allow adsorption to take place. Then, the column was washed with 4-fold column volume of 50 mM Tris-HCl/500 mM KCl (pH8.0) solution, supplied at the same flow rate, and the adsorbed protein then was eluted with 5-fold column volume of 50 mM Tris-HCl/2M KCl/0.01% (w/v) Tween 80 (pH8.0) solution Then, to fractions of the eluate from the Blue sepharose 6FF column was added an equivalent volume of 4M NaCl solution to adjust their salt concentrations. The solution was loaded on Phenyl sepharose HP column (column volume; about 6 L, bed height; about 20 cm) which had been equilibrated with 4-fold column volume of 50 mM Tris-HCl/2M NaCl (pH8.0) solution, supplied at a linear flow rate of 60 cm/hr, to allow adsorption to take place. Then, the column was washed with 4-fold column volume of 50 mM Tris-HCl/2.5 M NaCl (pH8.0) solution, supplied at the same flow rate, and the adsorbed protein was eluted with 5-fold column volume of 50 mM Tris-HCl/1.6 M NaCl (pH8.0) solution.

Figure 7:
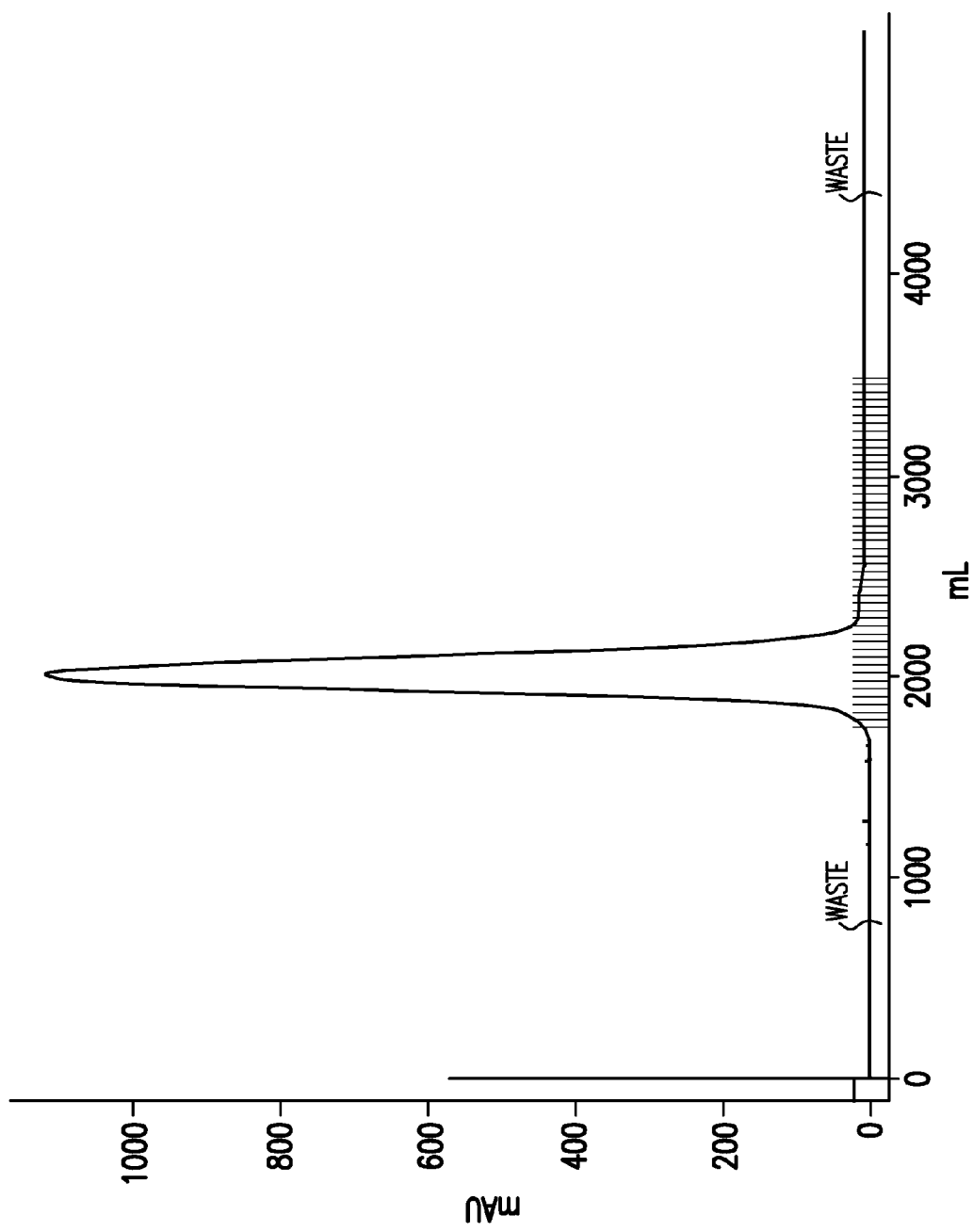
FIG. 7 shows the optical density pattern at 280 nm recorded in the gel filtration column chromatography.

Then, fractions of the eluate from the above Phenyl sepharose HP column were sequentially concentrated with Biomax5 membrane (5 kDa cut off: Millipore). The concentrated solution was loaded on Superdex peptide 75 pg (column volume; about 4.8 L, bed height; about 60 cm) which had been equilibrated with 20 mM sodium phspate/133 mM NaCl/0.01% (w/v) Tween 80 (pH7.4) solution, supplied at a linear flow rate of 14.9 cm/hr, and fractions exhibited peak absorption at 280 nm (FIG. 7) were separated and recovered as purified human FSH.

The recovery rate of human FSH of each purification step is shown in Table 1, in which "FSH recovery rate/process" means the proportion of the recovered amount of human FSH to the amount of loaded human FSH in each process, and "FSH recovery rate/total" the proportion of the recovered amount human FSH in each process to the amount of the human FSH subjected to the purification processes at the start.

The amount of human FSH subjected to the cation-exchange chromatography, the first step of purification, was 2256.1 mg, and 1043.5 mg of human FSH was finally recovered, thus the recovery rate having reached 43.9%. The result shows that the method for purification described above enables to purify human FSH in high yield and in a large scale.

TABLE 1

Recovery rate and specific activity of human FSH of each purification process (Lot No. 1)

| Purification process | FSH loaded (mg) | FSH recovered (mg) | FSH recovery rate/process (%) | FSH recovery rate/total (%) |
|---|---|---|---|---|
| Cation-exchange column (CaptoMMC) | 2256.1 | 2199.6 | 97.5 | 97.5 |
| Dye affinity column (Blue Sepharose 6FF) | 2187.1 | 1772.4 | 81.0 | 78.6 |
| Hydrophobic column (Phenyl Sepharose HP) | 1636.7 | 1389.1 | 84.9 | 61.6 |
| Gel filtration column (Superdex peptide 75pg) | 1667.7 | 1043.5 | 59.4 | 43.9 |

[Analysis of Purified Human FSH]

Figure 8:
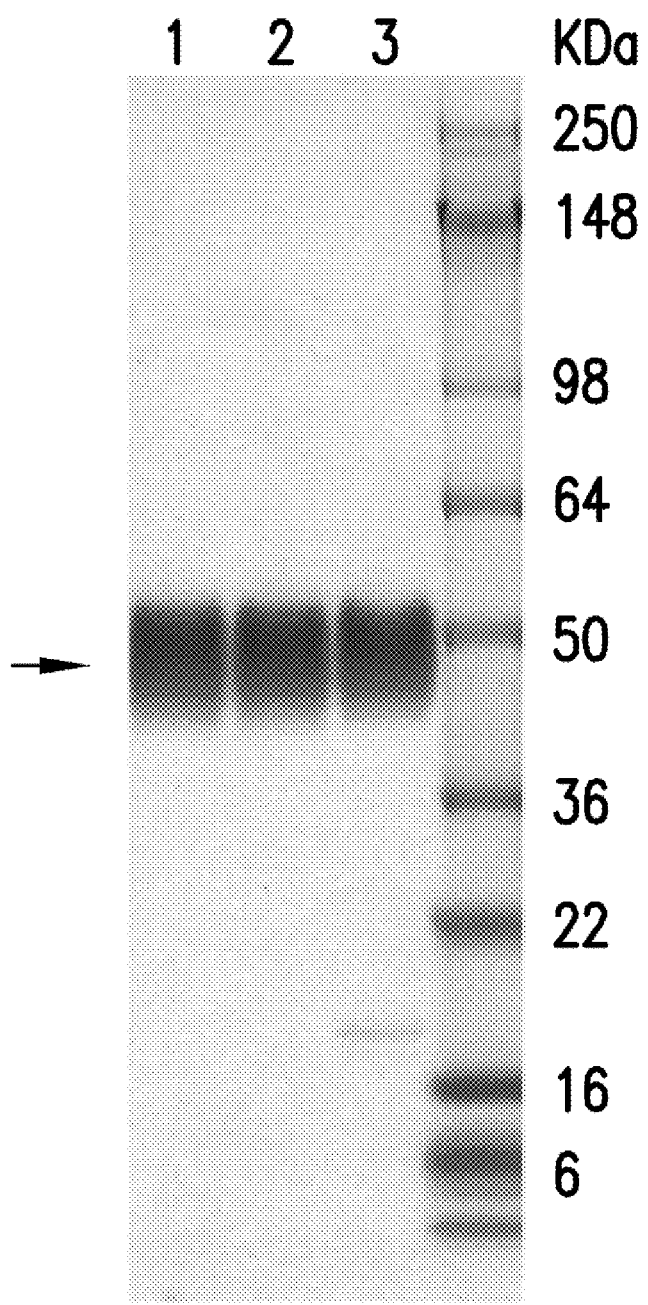
FIG. 8 shows the pattern obtained by SDS-PAGE gel electrophoresis of the purified human FSH under a non-reductive, non-heating condition. About 5 µg human FSH was applied to each lane. To the lanes 1-3 were applied the finally purified FSH of lot Nos. 1-3, respectively.

The human FSH purified above was subjected to SDS-PAGE electrophoresis under a non-reductive, non-heating condition. The gel stained with Coomassie blue revealed a single band alone at the position of molecular weight of about 45 kDa (FIG. 8). This band was stained by western blotting using an anti-human FSH antibody and was confirmed to be a band of human FSH (data not shown).

Figure 9:
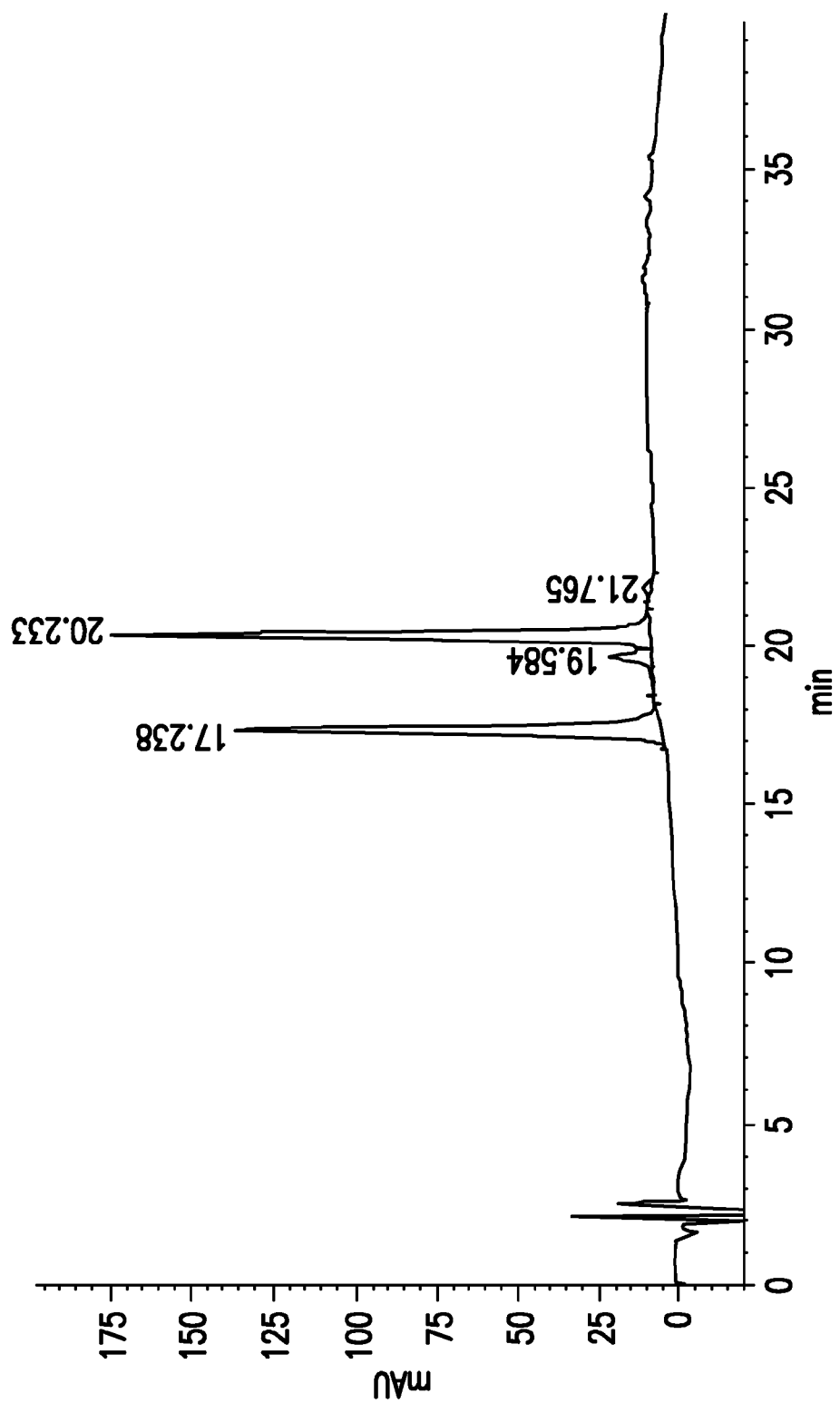
FIG. 9 shows an RP-HPLC chart of the purified human FSH (lot No. 1).

Further, RP-HPLC analysis of the above purified human FSH revealed that its was a highly purified human FSH, though in addition to peak 3 corresponding to the α chain and peak 1 corresponding to β chain, peak 2 was noticed which represented about 1% of the total area (FIG. 9). Analysis of its N-terminal amino acid sequence as well as of its amino acid composition revealed that this peak 2 was a peptide chain derived from the α chain.

Figure 10:
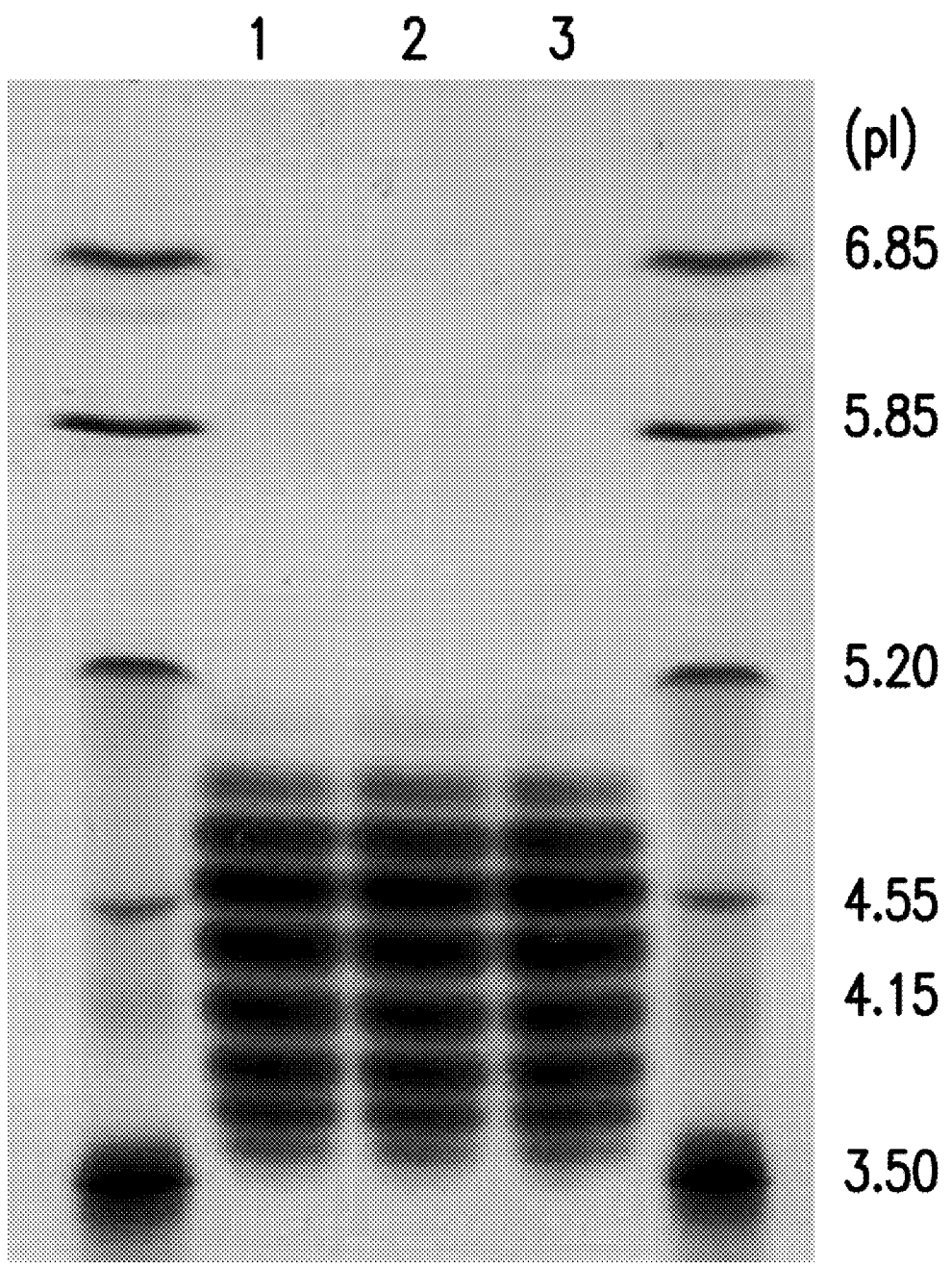
FIG. 10 shows the isoelectric focusing electrophoresis pattern of the purified human FSH. About 10 µg human FSH was applied to each lane. To the lanes 1-3 were applied the finally purified FSH of lot Nos. 1-3.

Furthermore, isoelectric focusing electrophoresis of the above purified human FSH showed multiple bands in the region of pI 3.5-5.5 (FIG. 10). This pattern was the same as an already reported pattern shown by isoelectric focusing electrophoresis of a recombinant FSH (Loumaye E., Human Reprod. Update 4: 862-881, 1998).

According to a measurement based on rat ovary weight increase, the specific activity of the above purified human FSH was 14,000-18,000 IU/mg. This value was comparable to or greater than the specific activity of the recombinant human FSH preparations already marketed as medical drugs in Japan (de Leeuw R., Mol. Hum. Reprod. 2: 361-369, 1996).

[Determination of Human FSH by ELISA]

To each well of a 96-well microtiter plate (Nunc) for EIA was added 100 µL of anti-human FSHα subunit antibody (Leinco Technologies) diluted to 1 µg/mL with 0.05M NaHCO$_3$ solution, and the plate was left undisturbed for at least 2 hours at room temperature to let the antibody be adsorbed. Then, after each well was washed three times with PBS containing 0.05% Tween 20 (PBS-T), 100 µL of the test sample or human FSH standard (Sigma), which had been diluted as desired with PBS containing 0.5% BSA and 0.05%

Tween 20 (PBS-BT), was added to the well, and the plate was left undisturbed for at least 2 hours at room temperature. Then, after each well was washed three times with PBS-T, 100 μL of PO-labeled anti-human FSHβ chain antibody (Leinco Technologies) which had been diluted 1000-fold with PBS-BT, and the plate was left undisturbed for at least 2 hours at room temperature. Each well then was washed three times with PBS-T, and 100 μL of a substrate solution was added to each well to let the enzyme reaction proceed at room temperature. The substrate solution was a buffer solution prepared by mixing 0.025M citric acid and 0.05M $Na_2HPO_4$ and adjusted to pH5.0 to which was added 0.4 mg/mL o-phenylenediamine (OPD) and 0.008% $H_2O_2$. Then, 100 μL of 2N $H_2SO_4$ was added to each well to terminate the reaction, and the optical density at 492 nm was measured for each well on a 96-well plate reader.

[Analysis of Human FSH by RP-HPLC]

High performance liquid chromatography was performed using LC-20A System, SPD-20AV UV/VIS Detector (Shimazu Corp.). TSKgel Octadecyl-4PW (4.6 mm×150 mm, Tosoh Corp.) was equilibrated with 4% acetonitrile solution containing 0.1% trifluoroacetic acid. The sample was loaded on this and eluted by linearly increasing the concentration of acetonitrile from 4% to 18%. For detection, optical density at 214 nm was measured.

[Measurement of Human FSH by Rat Ovary Weight Increase Method]

The measurement of the activity of human FSH was carried out by rat ovary weight increase method (Steelman S., Endocrinology 53(6): 604-616, 1953). Female SD rat of about 45-65 g body weight (Charles River Japan) were purchased and kept for 3 day for habituation. The test sample, or the human FSH standard, diluted to 0.2 mL with a sample diluent solution was subcutaneously administered to the rats in the afternoon of day 1, and before noon, at noon and in the afternoon of day 2, and then before noon and in the afternoon of day 3, thus 6 times in total. On day 5, the ovaries of the rats were taken out and their weight measured. The human FSH standard employed was "First international standard for Follicule Stimulating Hormone, (FSH) Recombinant, Human for Bioassay; NIBSC code 92/642; WHO". The sample diluent solution was prepared by dissolving 3 ampules of a hCG preparation (10000 IU, Japan Pharmacopoeia) in 2 mL/ample of the solvent attached (5000 IU/mL), and adding 4.0 mL of the solution thus obtained and 3.0 g bovine serum albumin to a proper volume of phosphate buffer (pH7.1) to dissolve, and then adjusting the volume of the solution to 250 mL with the buffer, and filtering the solution thus obtained with a 0.22 μm membrane filter. After its titer was estimated by administering to 5 rats/group the test sample which had been diluted at four different dilution rates, the main test was performed. In the main test, human FSH activity was determined according to the 2-2 dose test using 10 animals/group, with the high concentration group being set at the dilution rate at which the ovary weight was expected to become 95-105 mg, and with the low concentration group being set at the dilution rate that was 1.5-2 times dilution rate of the high dose group.

INDUSTRIAL APPLICABILITY

The method for production of recombinant human FSH according to the present invention enables to prevent viral contamination employing serum-free media in culturing recombinant human FSH producing mammalian cells, and it also enables to purify the expressed recombinant human FSH in high yield and to such a high purity that allows its direct use as a medicament. Therefore, the present invention is highly useful as a method for production of recombinant human FSH.

Sequence Listing
GP120.ST25

The entire disclosure[s] of all applications, patents and publications, cited herein and of corresponding JP application No. P2008-129254, filed May 16, 2008 and are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions

We claim:

1. A method for production of recombinant human follicle-stimulating hormone (FSH) comprising
   (a) transfecting Chinese hamster ovary (CHO) cells with a first expression vector comprising a polynucleotide encoding the α-subunit of human FSH and a second expression vector comprising a polynucleotide encoding the β-subunit of human FSH, wherein said first and said second polynucleotides are under the regulation of an EF-1α promoter;
   (b) culturing said cells of (a) in a serum-free medium under conditions sufficient for the production of recombinant human FSH;
   (c) collecting culture supernatant by removing the cells from the culture that is obtained in step (b);
   (d) subjecting the culture supernatant collected in step (c) to cation-exchange column chromatography, wherein the cation exchanger employed in said cation-exchange column chromatography is a weak cation exchanger having a selectivity based on both hydrophobic interaction and hydrogen formation, and wherein the culture supernatant is loaded on the column and washed with a phosphate buffer of pH 5.0-6.5 supplemented with 50-250 mM of a salt;
   (e) eluting the recombinant human FSH from the column by increasing the concentration of said salt in said buffer to 300-900 mM to obtain one or more recombinant human FSH fractions;
   (f) subjecting the fractions collected in step (e) to dye affinity column chromatography to collect recombinant human FSH-active fractions, wherein the column used for the dye affinity column chromatography is a triazine dye affinity column, and wherein the fractions collected in step (e) are adjusted to or near the neutral pH with a buffer prior to application to the triazine dye affinity column equilibrated with a buffer at or near neutral pH;
   (g) eluting recombinant human FSH from the triazine dye affinity column of step (f) with a buffer having an elevated salt concentration of 1.8-2.2 mol/L;
   (h) subjecting the fractions collected in step (g) to hydrophobic column chromatography to collect recombinant human FSH-active fractions, wherein the column used for the hydrophobic column chromatography is a Phenyl-Sepharose column adjusted to or near the neutral pH with a buffer supplemented with 2-3 mol/L of a salt, and wherein the fractions collected in step (g) are adjusted to a salt concentration of 2.5-3.5 mol/L prior to application to the Phenyl-Sepharose column;
   (i) eluting the recombinant human FSH from the phenyl-Sepharose column by decreasing the concentration of said salt; and
   (j) subjecting the fractions collected in step (i) to gel filtration column chromatography to collect recombinant human FSH-active fractions.

2. The method according to claim 1, wherein the weak cation exchanger comprises one or more phenyl groups, amide bonds or carboxyl groups.

3. The method according to claim 1, wherein the dye employed in the dye affinity column chromatography is a blue triazine dye.

4. The method according to claim 3, wherein the pH of the buffers in triazine-dye affinity chromatography of step (f) is 7.8-8.2.

5. The method according to claim 3, wherein the pH of the buffers in hydrophobic column chromatography of step (h) is 7.8-8.2.

6. The method according to claim 4, wherein the pH of the buffers in hydrophobic column chromatography of step (h) is 7.8-8.2.

7. A method for the production of recombinant human follicle-stimulating hormone (FSH) comprising
   (a) transfecting a mammalian cell with a first expression vector encoding the α-subunit of human FSH and a second expression vector encoding the β-subunit of human FSH, wherein said first and said second expression vectors are under the regulation of EF 1-α promoter;
   (b) culturing said mammalian cells in a serum-free medium under conditions sufficient for the production of said α-subunit of FSH and said β-subunit of FSH;
   (c) obtaining the culture supernatant by removing the cells from step (b);
   (d) subjecting the culture supernatant collected in step (c) to cation-exchange column chromatography and collecting a first batch of recombinant human FSH-active fractions;
   (e) subjecting the fractions collected in step (d) to dye affinity column chromatography and collecting a second batch of recombinant human FSH-active fractions;
   (f) subjecting the fractions collected in step (e) to hydrophobic column and collecting a third batch of recombinant human FSH-active fractions; and
   (g) subjecting the fractions collected in step (f) to gel filtration column chromatography and collecting a fourth batch of recombinant human FSH-active fractions.

* * * * *